(12) United States Patent
Mussivand

(10) Patent No.: US 6,346,071 B1
(45) Date of Patent: Feb. 12, 2002

(54) INFLOW CONDUIT ASSEMBLY FOR A VENTRICULAR ASSIST DEVICE

(75) Inventor: Tofy Mussivand, Navan (CA)

(73) Assignee: World Heart Corporation, Nepean (CA)

(*) Notice: Subject to any disclaimer, the term of this patent is extended or adjusted under 35 U.S.C. 154(b) by 0 days.

(21) Appl. No.: 09/354,801

(22) Filed: Jul. 16, 1999

(51) Int. Cl.[7] ............................................. A61M 1/12
(52) U.S. Cl. ...................................................... 600/16
(58) Field of Search ........................ 600/16–17; 604/4; 128/899

(56) References Cited

U.S. PATENT DOCUMENTS

| | | | |
|---|---|---|---|
| 4,104,005 A | | 8/1978 | Poirier |
| 4,508,535 A | | 4/1985 | Joh et al. |
| 5,511,958 A | | 4/1996 | Chen et al. |
| 5,755,784 A | * | 5/1998 | Jarvik ............................ 623/3 |
| 5,810,708 A | | 9/1998 | Woodward et al. |
| 5,964,694 A | * | 10/1999 | Siess et al. .................... 600/17 |

OTHER PUBLICATIONS

Sugita et al., "In Vivo Evaluation of a Permanently Implantable Thermal Ventricular Assist System" vol. XXXII Trans Am Soc Artif Intern Organs, 1986, pp. 242–247.

Blubaugh, A.L., Development of An Implantable Integrated Thermally Powered Ventricular Assist System, vol. I, Technical Proposal N85–2, Dec. 12, 1985, pp. 1–322.

Olan, R.W., "National Heart, Lung, and Blood Institue Division of Heart and Vascular Diseases Contract No. N01–HV–28002" Quarterly Report, 1986, pp. 1–76.

* cited by examiner

Primary Examiner—William E Kamm
(74) Attorney, Agent, or Firm—Killworth, Gottman, Hagan & Schaeff, L.L.P.

(57) ABSTRACT

An inflow conduit assembly for conducting blood from a ventricle to a Ventricular Assistance Device (VAD) is provided. The assembly includes a rigid tube including an angled heart engaging end for insertion into a ventricle. The angled heart engaging end defines a long side for placement adjacent a heart septum. The tube includes an orifice end for attachment to the VAD, and the inflow conduit assembly further includes a coupling for attaching the orifice end of the tube to the VAD. The coupling is movable between a rotatable position wherein the tube is rotatable relative to the VAD, and a locked position wherein the tube is immobile relative to the VAD.

15 Claims, 9 Drawing Sheets

INFLOW CONDUIT ASSEMBLY FOR A VENTRICULAR ASSIST DEVICE

FIELD OF INVENTION

The present invention relates to mechanical circulatory devices, and in particular to a conduit for a ventricular assist device.

BACKGROUND OF THE INVENTION

Mechanical Circulatory Devices (MCDs) such as artificial hearts, Ventricular Assist Devices (VADs) and other blood circulating systems have become increasingly recognized as life saving devices for patients whose heart is diseased or has been injured by trauma or heart attack or other causes. VADs in particular, are recognized as a major life saving modality for assisting patients who suffer from congestive heart failure.

VADs must be connected to the natural heart of patients. In order to connect a VAD to a natural heart of a patient, a conduit assembly is used. The conduit assembly has a tubular tip body. The tip body is inserted into the heart. For proper functioning, the tip body should penetrates the heart wall so that the tip of the tip body comes out of the heart wall. If the tip body does not penetrate long enough, the heart muscle tissue surrounding the open end of the tip body grows and closes over the opening of the tip body. Thus, the blood flow is blocked.

By penetrating the heart wall, the closing of the opening of the tip body by the heart muscle may be avoided. However, the penetrated tip body may interfere with the septum wall separating two blood chambers of the natural heart. The septum wall may interfere the blood flow coming into the opening of the tip body, and in a worst case, it could totally close the opening of the tip body.

Therefore, there is a need of a tip body for a conduit assembly which can prevent such interference of the septum wall of the heart.

SUMMARY OF THE INVENTION

According to the invention, an inflow conduit assembly for conducting blood from a ventricle to a VAD having an orifice surrounded by an orifice Rim includes a rigid tube. The rigid tube includes an angled heart engaging end for insertion into a ventricle. The angled heart engaging end defines a long side for placement adjacent a heart septum. The angled heart engaging end has an outer surface defining at least one hole for draining blood from the ventricle.

According to one aspect of the invention, the tube includes an orifice end for attachment to the VAD, and the inflow conduit assembly further includes a coupling for attaching the orifice end of the tube to the VAD. The coupling is movable between a rotatable position wherein the tube is rotatable relative to the VAD, and a locked position wherein the tube is immobile relative to the VAD.

BRIEF DESCRIPTION OF THE DRAWINGS

The present invention will be further understood from the following detailed description, with reference to the drawings in which.

Similar references are used in different figures to denote similar components.

DETAILED DESCRIPTION OF THE INVENTION

Mechanical Circulatory Devices (MCDs) include artificial hearts and Ventricular Assist Devices (VADs). An artificial heart is used in place of a natural heart. A VAD is used where a patient's natural heart that is diseased or injured is still partially functioning. A VAD is connected to such a natural heart and assists its functioning. Hereinafter the present invention is mainly described referring to VADs. However, the invention may be also applied to artificial hearts, other than those aspects respecting to connection with a natural heart.

Figure 1:
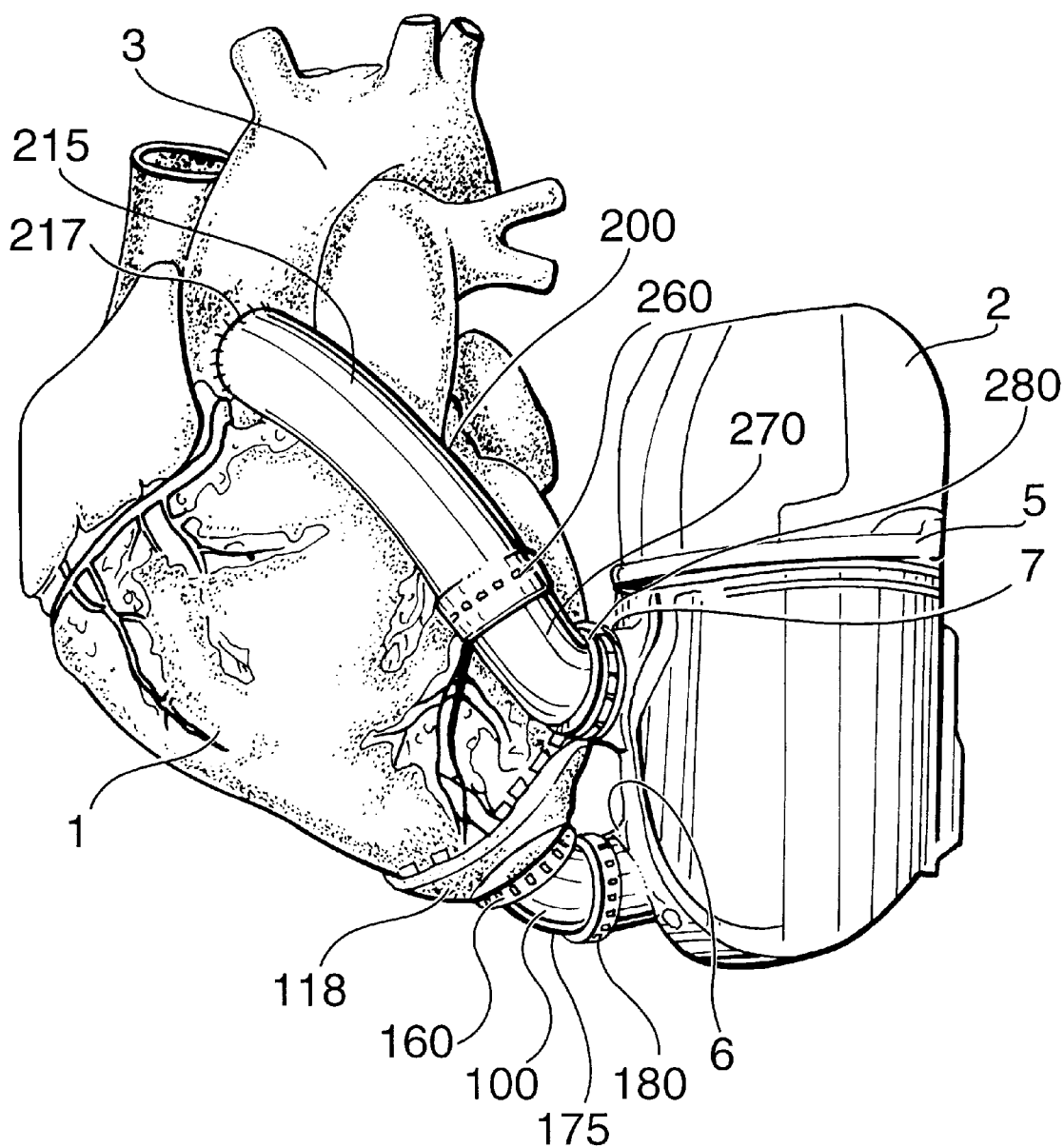
FIG. 1 is a schematical side view of a VAD in use to which an embodiment of the present invention is applied.

FIG. 1 shows a VAD 2 in use to which an embodiment of the present invention is suitably applied. The VAD 2 has a blood chamber 5 having an inflow orifice 6 and an outflow orifice 7. At the inflow orifice 6, an inflow conduit assembly 100 is provided to connect the blood chamber 5 to a natural heart 1 of a patient. At the outflow orifice 7, an outflow conduit assembly 200 is provided to connect the blood chamber 5 to the thoracic aorta 3. The outflow conduit assembly 200 may be connected to a different part of the blood circulation system.

In operation, blood is pumped from the heart 1 into the blood chamber 5 of VAD 2 through the inflow conduit assembly 100. The VAD 2 then pumps the blood out of the blood chamber 5 into the thoracic aorta 3 through the outflow conduit assembly 200.

The inflow conduit assembly 100 comprises one or more conduits or tubes. A proximal tube 175 that is connected to the inflow orifice 6 is made to be rigid to provide strength and durability of the conduit assembly 100. The proximal tube 175 is preferably curved to minimize interference with adjacent organs. In order to connect such a curved rigid tube 175, the conduit assembly 100 uses a coupling 180 which is movable between a rotatable position and a locked position. In the rotatable position, the proximal tube 175 can be rotated about its axis relative to the VAD 2 so that it can be positioned at a desired angle to avoid interference with adjacent organs. The axis of the proximal tube 175 curves as the tube 175 covers. The tube 175 rotates about the axis at the section engaging with the VAD 2. The VAD 2 may have one or more extension tubes. In that case, the tube 175 rotates about the axis at the section engaging with the nearest extension tube. After the angle of the proximal tube 175 is decided, the coupling 180 is moved to the locked position so that the proximal tube 175 is immovably locked relative to the VAD 2. Similar couplings are used for connection of other components as described later.

Figure 2A:
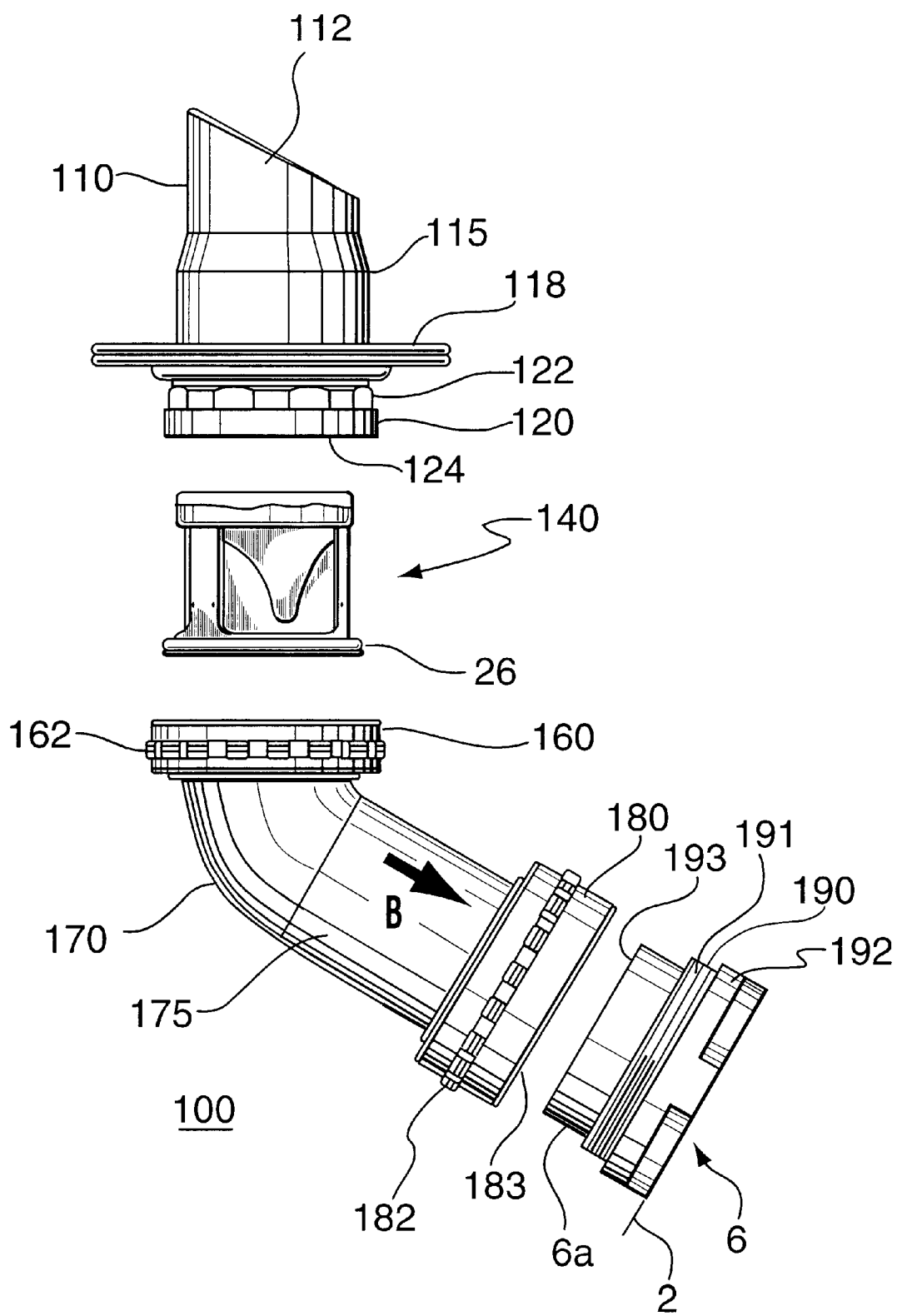
FIG. 2A illustrates a lateral, exploded view of an inflow conduit assembly in accordance with an embodiment of the invention.

FIG. 2A shows a lateral exploded view of the inflow conduit assembly 100 in accordance with an embodiment of the invention. In this embodiment, the inflow conduit assembly 100 is connected to the VAD 2 by a coupling comprising a gland nut 180 and a corresponding threaded connector 191.

The inflow conduit assembly 100 comprises two basic components, an apical tip assembly 110 and an inflow elbow assembly 170. The apical tip assembly 110 and the inflow elbow assembly 170 are adapted to be connected together.

The inflow conduit elbow assembly 170 comprises an inflow elbow tube or conduit 175 with a female threaded coupling or gland nut 160 at one end and a further female threaded gland nut 180 at the other end.

The inflow elbow conduit 175 is rigid and generally curved along its length. Its shape is dictated by the desire of minimizing interference with adjacent organs. The inflow elbow conduit 175 presented in FIG. 2A has only one bend, however other shapes such as an S-shaped inflow elbow conduit may also be used.

On the VAD 2, an inflow plug 190 is mounted at the inflow orifice 6. The inflow plug 190 comprises an inflow port extension 6a having a rim 193 and a male threaded connector 191 for coupling to the gland nut 180. The inflow plug 190 also has a flange 192 on its base surface near the inflow orifice 6. The flange 192 has a cross-shaped outer surface. It serves in gripping onto the inflow plug 190 when the gland nut 180 is being tightened.

The gland nut 180 provides a rotatable union effect during the fitting procedure. That is, the gland nut 180 moves between a rotatable position and a locked position. At the rotatable position, the gland nut 180 allows the inflow elbow conduit 175 to rotate about its axis into any rotated position relative to the VAD 2, when the VAD 2 is implanted. This allows flexibility in positioning of the conduit assembly 100. The positioning flexibility is advantageous, considering the difference in anatomies from patient to patient. The positioning flexibility is also useful during experiments performed on calves, for example, which present even a more dramatic difference in anatomy by comparison to the human anatomy. During the fitting of the VAD 2, an optimal position for the inflow elbow conduit 175 is determined. Then, the inflow elbow conduit 175 is locked in this position by tightening the gland nut 180 to the locked position. The optimal position of the inflow elbow conduit 175 defines a predetermined way into which the inflow conduit is to be fitted within its anatomical environment.

In order to achieve tight sealing, it is preferable that an end 183 of the inflow elbow conduit 175 closely mates the rim 193 of the inflow port extension 6a. One or more sealing rings may be used between the rim 193 of the inflow port extension 6a and the end 183 of the inflow elbow conduit 175 for tight sealing.

In order to facilitate the rotation of the inflow elbow conduit 175, it is preferable that the mating surfaces of rim 193 of the inflow port extension 6a and the end 183 of the inflow elbow conduit 175 are smooth. It is also preferable that the rim 193 of the inflow port extension 6a and the end 183 of the inflow elbow conduit 175 are flat in a plane perpendicular to the axis of the inflow elbow conduit 175. It is also preferable that they have coincidental circular shapes so that the inflow elbow conduit 175 may be rotated at any desired angle. However, they may have unsmooth surfaces, such as a saw like shape, or non-circular shapes, such as octagonal shapes, as long as those surfaces can achieve desired sealing effects at different rotational angles, with or without the aid of other sealing member.

The gland nut 180 may include bulges 182 on its external envelope surface. One of the purposes of the bulges 182 is to aid in gripping, by hand or by a wrench, onto the nuts 180, during the fitting procedure. An alternative embodiment contemplates small cavities or holes instead of the bulges, to be gripped by a special instrument. Such an embodiment may be preferred because of the edges on the bulges 182.

The gland nut 180 is preferably manufactured to very high tolerances to ensure an extremely smooth seam between the component pieces. A biolization coating is added, to make the seam as non-thrombogenic as possible.

Figure 6:
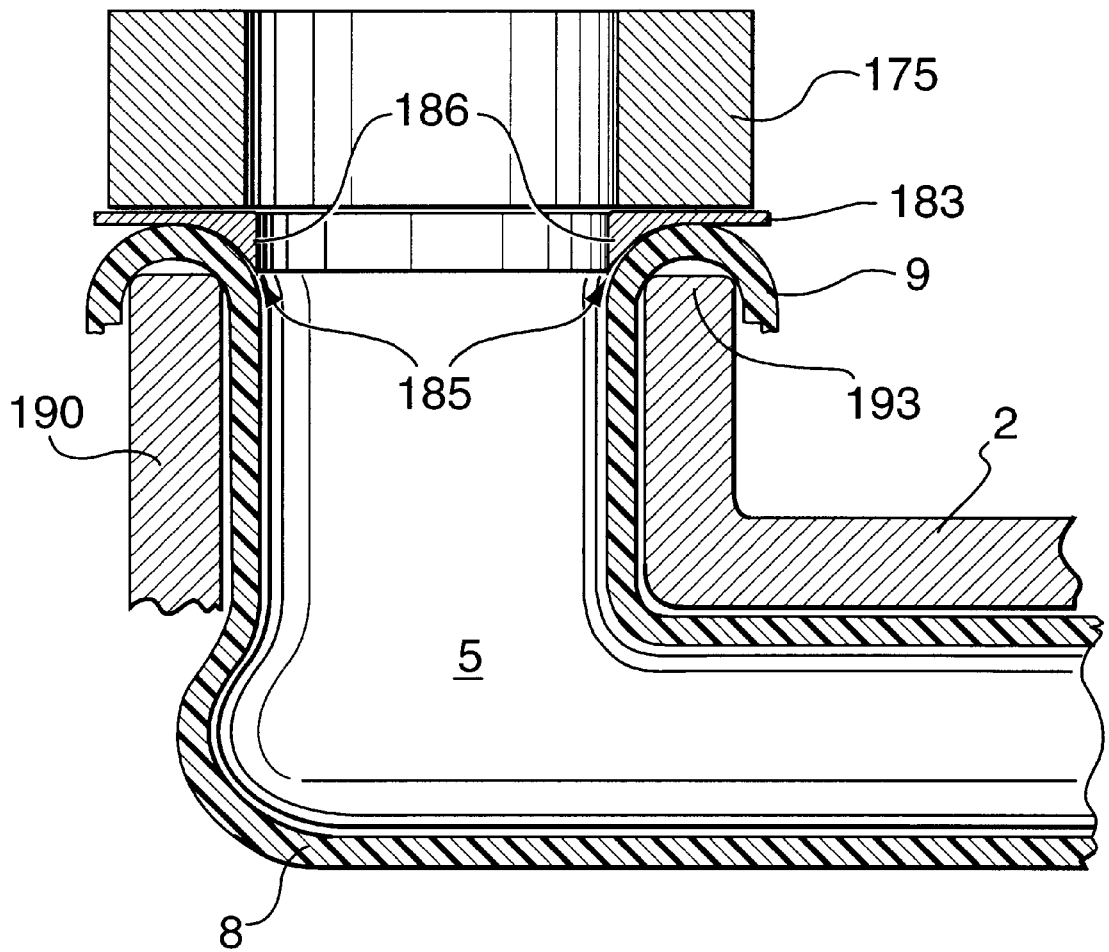
FIG. 6 is a partial cross-sectional view of the inflow elbow conduit.
Figure 7:
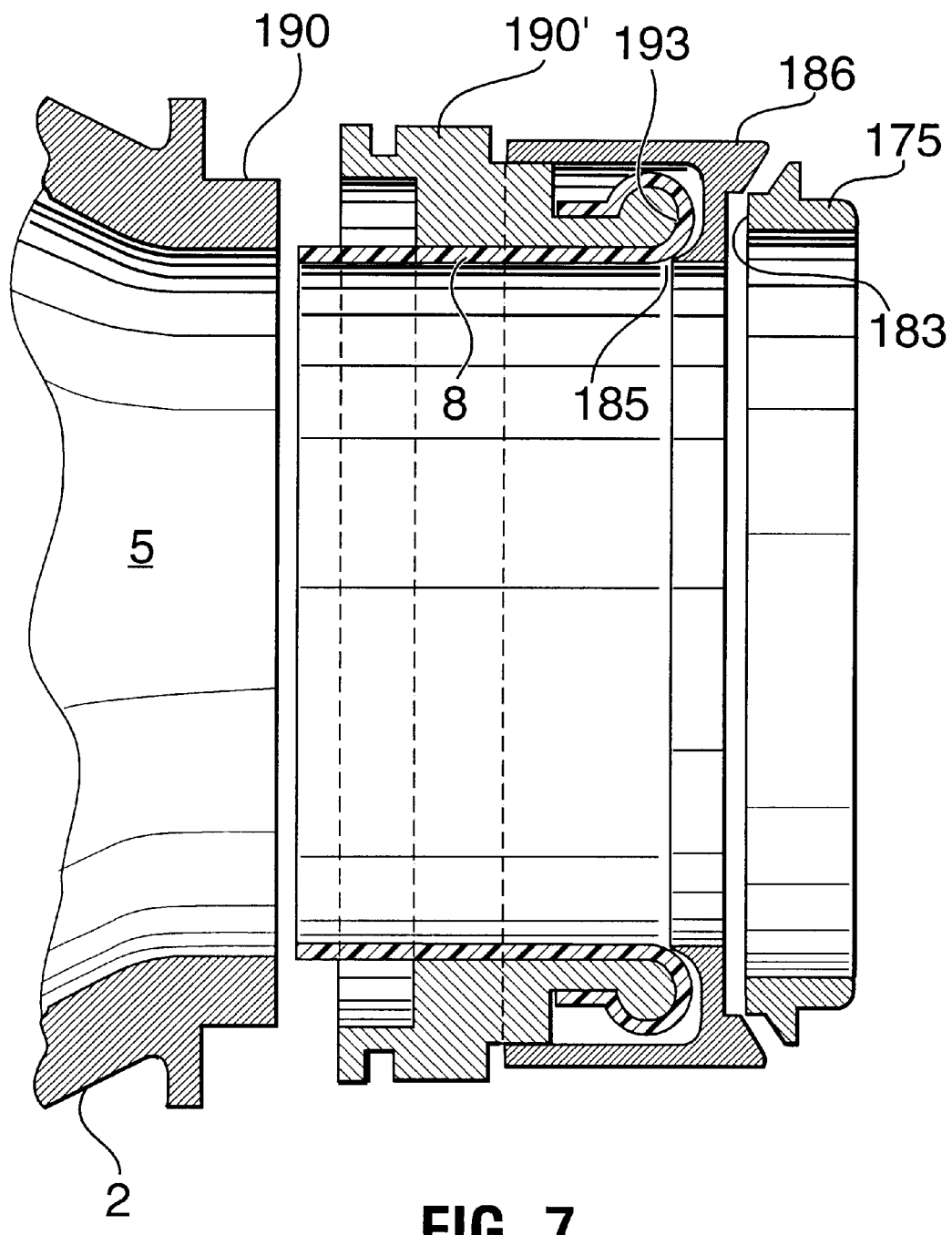
FIG. 7 is a partial cross-sectional view of another inflow elbow conduit.

As shown in FIG. 6, it is common that the VAD 2 uses an elastic bag 8 to form the blood chamber 5. It is preferable to extend the open end 9 of the elastic bag 8 over the rim 193 of the inflow port extension 6a to prevent leakage of blood from the open end 9. The bended open end 9 is held by the engaging surface 183 of the inflow elbow conduit 175. In order to provide a constant blood flow, the inner diameter of the elbow conduit 175 is adjusted to be smaller than that of the inflow plug 190 for twice of the thickness of the elastic bag 8. By adjusting the inner diameter of the elbow conduit 175, the inner wall of the elbow conduit 175 may be aligned with the inner surface of the elastic bag 8. However, in this arrangement, due to the thickness of the elastic bag 8, the elastic bag 8 creates a ring space 185 having a semi triangle cross sectional shape is created at the bended corner of the elastic bag 8. This space 185 tends to cause turbulence in the blood flow. In order to prevent such turbulence, it is preferable to provide a washer 186 to mask the space 185.

Referring back to FIG. 2A, the apical tip assembly 110 comprises a tubular tip body 112, a skirt 118 and an end section 120. The tubular tip body 112 is designed for insertion into the heart of the patient. The end section 120 is designed to stay outside the heart. The tip assembly 110 is sutured to the heart by the skirt 118.

Figure 3:
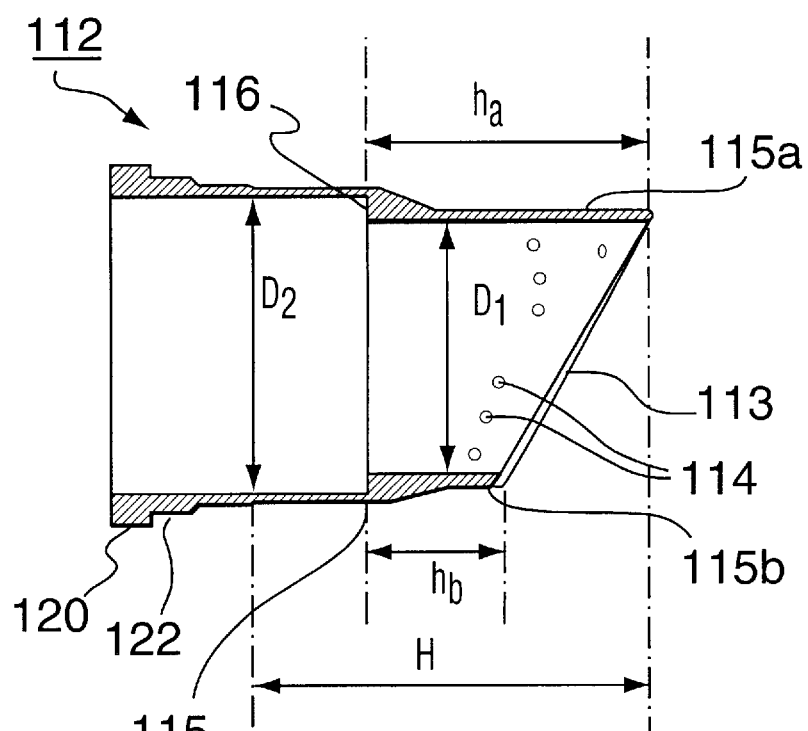
FIG. 3 is a lateral cross-section of the tip body of the inflow conduit assembly in FIG. 2A.

FIG. 3 is a lateral cross-sectional view of the tip body 112. The tip body 112 has a tip section 115. The tip section 115 is preferably rigid for insertion into the natural heart 1 through the heart muscle as shown in FIG. 1. The length H of the tip body 112 is selected to be long enough to protrude the cardiac tissue of the heart wall, but not interfere with the heart muscle pumping action.

For proper functioning, the length H of the tip section 115 is preferably larger than the thickness of the heart wall through which it penetrates. If the tip body 112 is too short and it does not protrude the heart wall, the heart muscle tissue surrounding the open end of the tip body 112 grows and closes over the opening of the tip body 112, thereby blocking the flow of blood from the heart. Based on human and animal experiments and observations, this length H is preferably between 1.5 and 3.5 cm. The inside diameter of the tip body 112 must allow sufficient blood flow to pass with acceptable velocities. If it is too slow, the blood flow can cause low washout. If it is too fast, the blood flow is disturbed causing turbulence. In order to let sufficient flow discharge for various body sizes and activities, a diameter $D_1$ of 13 to 30 mm is recommended. The smaller end of the range may be suitable for small body sizes, and the larger one for larger body sizes.

The protruding tip section 115 has the above advantages. However, it tends to cause blood pooling around the protruding tip section 115. That is, around the tip section 115 near the hart wall, the blood flow becomes stagnant. In order to reduce such blood pooling, it is preferable to provide the tip section 115 with drainage holes 114 on its wall. The size of the holes 114 is such that the blood flows therethrough without clotting. It is preferably approximately 3 mm. The holes are preferably spaced approximately at a regular distance around the circumference of the tip section 115. They may be provided approximately at every centimeter around the circumference of the tip section 115. The provision of the holes 114 prevents or reduces the risk of stasis and thrombosis.

It is preferable that the open end 113 of the tip section 115 is angled relative to the axis of the tubular tip body 112. Thus, the tip section 115 has a longest side 115a having a length $h_a$ and a shortest side 115b having a length $h_b$, as shown in FIG. 3. If the open end 113 of the tip section 115 is flat in a plane perpendicular to the axis of the tip section 115, the septum wall separating two blood chambers of the natural heart may interfere the flow of blood, and it could totally close the opening of the tip section 115. By angling the open end 113, such interference by the septum wall can be avoided.

When implanting the VAD assembly, the tip section 115 is fitted to rest with the longest side 115a against the septum wall of the heart. Thus, the longest side 115a is defined as the septum wall of the VAD assembly. The shortest side 115b of the tip section 115 is defined as the free wall.

In order to properly align the tip section 115, the tip assembly 110 further includes a male threaded connection 120 which forms a union coupled with the female threaded gland nut 160 of the inflow elbow assembly 170 as shown in FIG. 2A. The gland nut 160 is similar to the gland nut 180 described above. By the gland nut 160 and the male threaded connection 120, the tubular tip body 112 and the inflow elbow conduit 175 are rigidly fixed to one another in any relative angular position. The gland nut 160 may include bulges 162 on its external envelope surface, similar to the bulges 182 on the gland nut 180.

It is preferable that the tip body 112 accommodates a valve inset or assembly 140 to regulate the blood flow as described below. In order to accommodate the valve assembly 140 without generating disturbance in the blood flow, it is preferable that the tubular apical tip body 112 is cylindrical and presents a variable internal cross-section such that an essentially constant blood flow diameter is achieved when all parts of the conduit assembly arc fitted together. The tip body 112 may comprise two sections of internal diameters $D_1$ and $D_2$, respectively, as shown in FIG. 3. An internal ridge 116 may be provided to achieve the change in the internal cross-section. Referring also to FIG. 2A, the valve assembly 140 has an external diameter smaller than $D_2$ but larger than $D_1$. Thus, it slides into the enlarged elongated cylindrical opening within the apical tip body 112 up to the ridge 116. Preferably, the internal diameter of the valve assembly 140 is approximately equal to $D_1$, for achieving an essentially constant blood flow diameter. This is important for the prevention of clot formation in the conduit. From literature and experimental studies, it is seen that an absolute blood flow diameter close to 23 mm is well suited to optimize the prevention of effects leading to clotting.

The end section 120 of the tip body 112 may be provided with a hexagonal outer cross section 122. The hexed region 122 is intended to provide stability while fitting the VAD 2 inside the patient. Stability may be provided through a wrench action for example, so that the torque applied to the natural heart 1 during fitting is minimized.

The apical tip assembly 10 is attached to the natural heart 1 by means of the skirt 1118. The skirt 118 is mounted on the tip body 112 between the tip section 115 and the end section 120. The material from which the skirt 118 is manufactured is a flexible material, with tissue compatible characteristics. Many materials presenting such properties are known in the art. A commonly used material is a woven polyester velour. The shape of the skirt 118 may be circular or any other shapes. In a preferred embodiment, the skirt 118 is made of a flexible but strong material, it has approximately 1 to 12 cm in width. It is glued to the tip body 112 and sutured in place to the inside of the heart muscle. The procedure of suturing the skirt 118 is similar to that known in the art as ventricular apical cannulation. The skirt 118 is sufficiently flexible to conform to the curvature of the natural heart 1 and can be pierced with relative ease by a surgical needle. Once sutured in place, the heart tissue will grow and surround the skirt 118, thus making an extremely strong bond.

In the embodiment of FIG. 2A, the inflow conduit assembly 100 presents a completely rigid structure to blood flowing through it. The use of a rigid structure prevents the conduit from collapsing, breaking or twisting under the various compression, tensile, torque forces and negative pressures exerted upon it. While the embodiment of FIG. 2A has a completely rigid structure, it may also include an elastic tubular member when less pressures are exerted, e.g., between the tip assembly 110 and the elbow assembly 170. A diseased heart is generally swelled. Such a diseased heat tends to shrink as the disease is being cured. The elastic tubular member absorbs such changes in the size of the heart, and maintains the proper connection between the heart and the VAD 2.

As to the material of rigid components, it is preferable to use titanium for several reasons. There is evidence to support the idea that the use of titanium provides the conduit systems 100 and 200 with non-thrombogenic properties. Specifically, titanium, when exposed to oxygen, becomes titanium oxide, which is also believed to be non-thrombogenic. In order to improve the blood compatibility of titanium oxide, the interior surface of the conduit systems 100 and 200 may be coated with a gelatin coating. This technique is known as biolization.

Titanium is one of the strongest metals for its weight. It has proven to be durable, extremely strong and resistive to stress. Therefore, the use of titanium allows for the manufacturing of very thin conduits, of reduced size and small weight. The use of titanium for over 60 years in humans for such things as hip joints, finger joints, orthopaedics and prosthesis shows evidence of tissue compatibility and non-thrombogenic properties.

Figure 2B:
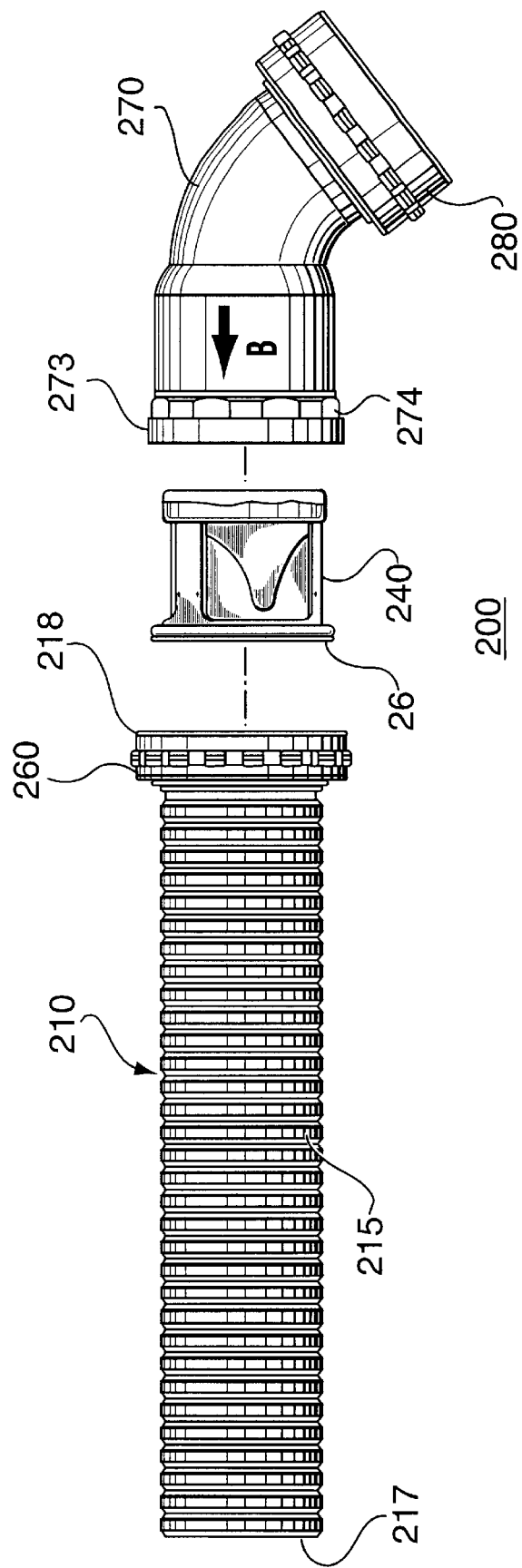
FIG. 2B illustrates a lateral, exploded view of an outflow conduit assembly in accordance with an embodiment of the invention.

Referring now to FIG. 2B, the outflow conduit assembly 200 comprises two basic components, an outflow conduit 210 and an outflow elbow assembly 270, adapted to be connected together. Blood flows through the assembly 200 as shown by arrow B.

In the embodiment presented in FIG. 2B, the outflow conduit 210 comprises a tubular conduit section 215, having an outflow end 217 and an inflow end 218. The outflow end 217 is adapted to be sutured onto an artery or similar vessel. The inflow end 218 comprises a female threaded coupling or gland nut 260. The gland nut 260 is similar to the gland nut 180 of the inflow conduit elbow assembly 100 in FIG. 2A. The conduit section 215 is made of a flexible, tissue compatible material, such as a woven polyester velour. It is manufactured sufficiently long so that it can be cut at a desired length during the fitting procedure, either in a patient, or in an animal during experimental studies. Referring to FIG. 1, the outflow end 217 of the conduit section 215 is shown sutured to the thoracic aorta 3.

The outflow conduit elbow assembly 270 is rigid and similar to the inflow elbow assembly 170 in FIG. 2A. In the embodiment presented in FIG. 2B, the outflow conduit elbow assembly 270 includes a gland nut 280 at its inflow end, and a male threaded connector 273 at the other end. The gland nut 280 is similar in function to the gland nut 180 in the inflow conduit elbow assembly 170 in FIG. 2A. The gland nut 280 is adapted to be coupled to a plug provided on the VAD 2 at the outflow orifice 7, similar to plug 190. Thus, the outflow elbow assembly 270 may be rotated around the axis of the elbow conduit, and then fixed at a desired angle relative to the VAD 2. The male threaded connector 273 may include a hexagonal region 274 for gripping while tightening the gland nut 260. In addition, the elbow assembly 270 may further include an enlarged elongated cylindrical opening within it, to receive a valve assembly 240.

Preferably, the length and orientation of the components of the conduit systems 100 and 200 are chosen so as to minimize compression on adjacent organs and great vessels, once the MCD is implanted within an anatomical environment. Optimal sizes, geometries and orientations of the various parts of the conduit systems 100 and 200 may be determined based on study of both the literature and the anatomy of the human chest, as well as taking actual measurements during both intra-operative procedures and from fresh cadavers.

The outflow elbow assembly 270 may also include an enlarged elongated cylindrical opening similar to that in the apical tip assembly 110 shown in FIG. 2A for receiving a valve assembly 240.

Referring back to FIG. 2A, the valve assembly 140 having a one-way valve is provided in the tip assembly 110 of the inflow conduit assembly 100. The one-way valve assembly 140 prevents back flow of the blood from the blood chamber 5 to the heart. Traditionally, such a one-way valve was provided at the inflow orifice 6. However, it often generated undesired flow patterns in the blood flow. Compared to the inflow port location, within the conduit assembly 100, the blood flow is more stable. Thus, by providing the valve in the conduit assembly 100, the disturbance in the blood flow by the provision of the valve is reduced.

Similarly, the outflow conduit assembly 200 is provided with the valve assembly 240 having a one-way valve in the elbow conduit assembly 270, as shown in FIG. 2B. The valve assemblies 140 and 240 may be identical to each other. By using identical valve assemblies for the inflow and outflow conduit assemblies 100 and 200, these assemblies may be inserted in either conduit. This leads to an easier, more effective, fitting procedure. The valve assemblies will be described hereinafter referring only to valve assembly 140, for simplicity.

Figure 4A:
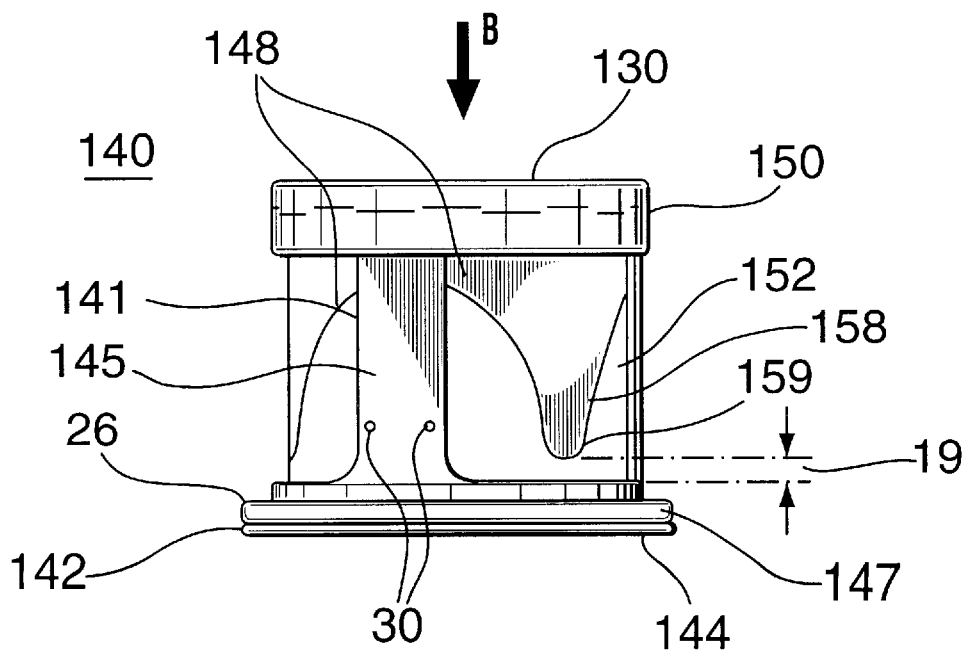
FIG. 4A is a lateral view of the valve assembly in accordance with an embodiment of the present invention.
Figure 5A:
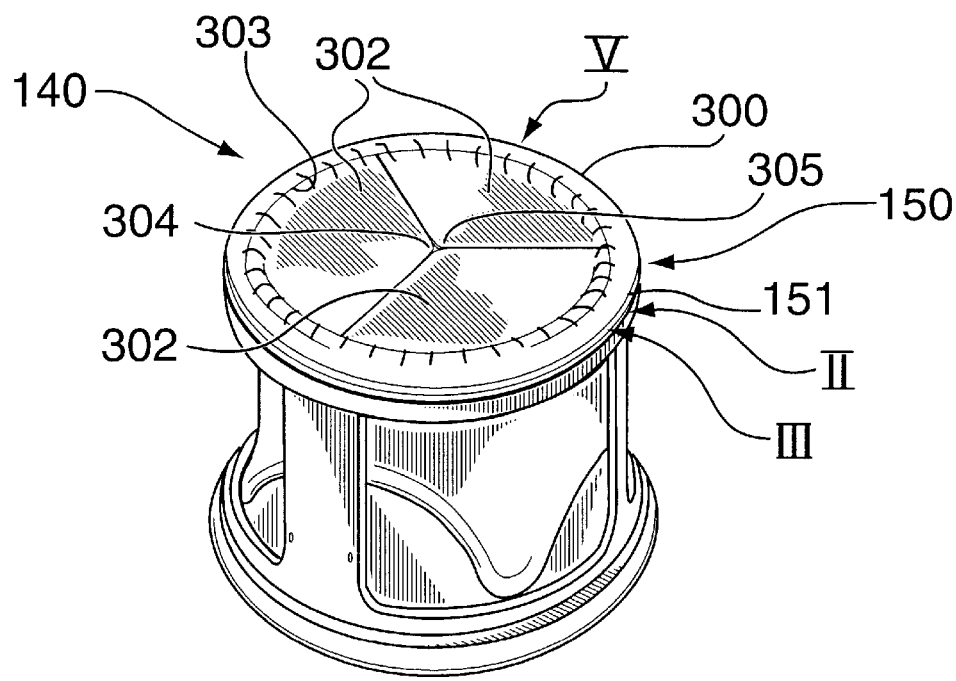
FIG. 5A is a perspective view of the inflow end of the valve assembly, depicting the suturing technique, in accordance with an embodiment of the invention.
Figure 5B:
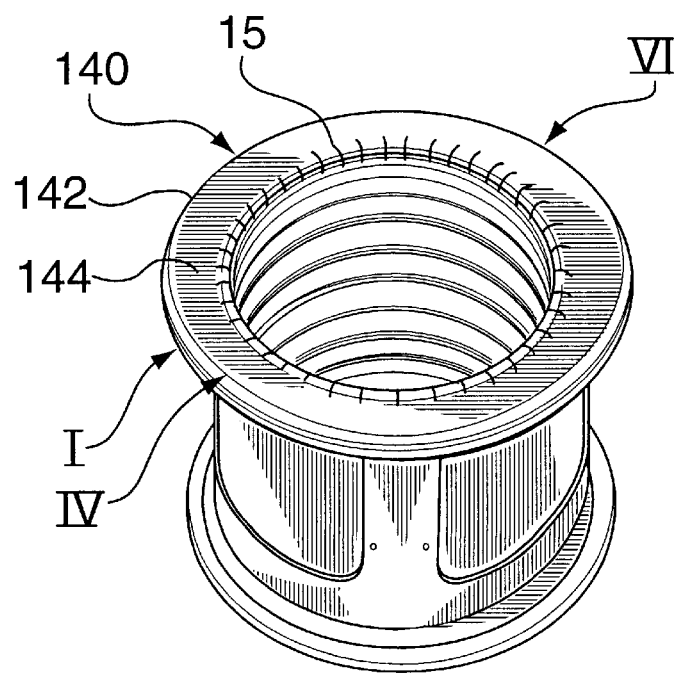
FIG. 5B is a perspective view of the outflow end of the valve assembly, depicting the suturing technique, in accordance with an embodiment of the invention.

Referring to FIGS. 4A, 5A and 5B, the valve assembly 140 comprises a valve enclosure assembly 141 and a one-way modified tissue valve 300. The valve enclosure assembly 141 comprises a valve enclosure 145, an outflow suture assembly 142 and an inflow suture assembly 150. The tissue valve 300 is sutured to the inflow suture assembly 150.

The modified tissue valve 300 is preferably a tricuspid or tri-foliate, having three leaflets 302. Each leaflet 302 has a semi-triangle shape having a semi-circular base end 303. The base end 303 is sutured on the inflow suture assembly 150. The other two ends 304, 305 of the leaflet 302 are free ends. Three leaflets 302 are provided so that each free ends 304, 305 is located closely to the free end 304, 305 of the neighboring leaflet 302. When the blood flow comes in the direction shown with the arrow B in FIG. 4A, the leaflets 302 open the spaces between the free ends 304, 305 by bending along the blood flow. When the blood flow comes in the other direction, the leaflets 302 close the spaces between the free ends 304, 305 to block the blood flow. Each leaflet 302 is preferably made of natural or artificial tissue.

While blood flows through the tissue valve 300, the leaflets 302 hits the walls of the conduit within which the valve 300 is mounted by their natural movements as dictated by the blood flow. The tip of the leaflets 302 is therefore impeded and repeatedly contacted against the wall. This may wear, deformation, and eventually tear in the leaflets 302.

In order to reduce the impacts on the leaflets 302, it is preferable to provide a movable wall 152. The movable wall 152 is attached onto the enclosure 145 by suturing assemblies 142 and 150.

The movable wall 152 is preferably made of a natural or artificial tissue material. Such material is preferably grafted on a flexible, blood compatible fabric 156, such as woven polyester velour, for further attachment within valve assembly 140.

Figure 4B:
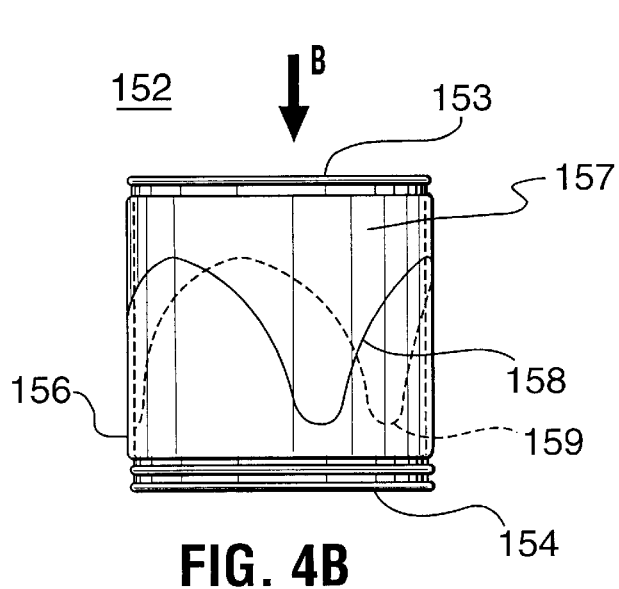
FIG. 4B is a lateral view of a modified tissue valve.

FIG. 4B shows the movable wall 152. The movable wall 152 has a wall annulus 157 bordered by a sinusoidal wall inset 158. The wall inset 158 forms three peaks 159, corresponding to the three leaflets 302 of the tissue valve 300. The wall inset 158 is made of a natural or artificial tissue material. Thus, the wall inset 158 may expand by the blood flow.

When blood flows through the tissue valve 300 as shown by arrow B in FIG. 4A, the movable wall 152 moves naturally as the wall inset 158 expands by the blood flow. The movement of the movable wall 152 occurs predominantly in a radial direction as the wall inset 158 is supported by the valve enclosure 145 and the wall annulus 157. The maximum radial deflection occurs at the points farthest from the center, which are at the peaks 159 of the wall inset 158. Thus, the tip of the leaflets 302 of the tissue valve 300 does not touch to the movable wall 152.

Figure 4C:
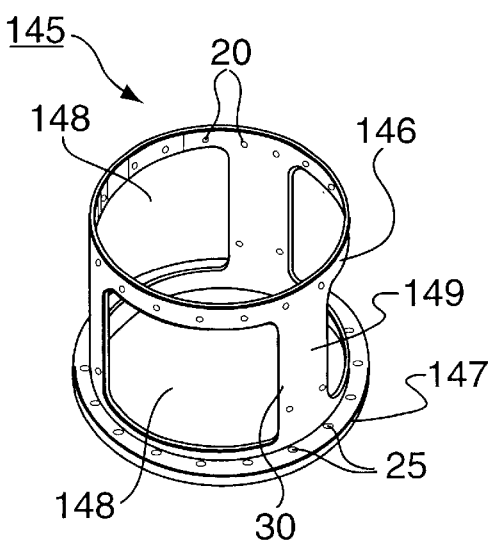
FIG. 4C is a perspective view of the valve enclosure in accordance with the embodiment in FIG. 4A.

FIG. 4C shows the valve enclosure 145. The valve enclosure 145 comprises a cylindrical body defined by an inflow base ring 146 in the plane of the cylinder, an outflow base ring 147 forming a flange at the base of the cylindrical body and three legs 149 joining the two rings to define three side windows 148. Preferably, the windows 148 are identical, located approximately 120° apart.

Referring to FIG. 4A, in accordance with a preferred embodiment of the invention, in assembling the valve assembly 140 the movable wall 152 is sutured onto the valve enclosure assembly 141 by positioning the three peaks 159 of the sinusoidal wall inset 158 in the centers of the three windows 148 of the valve enclosure 145, respectively. A preferred embodiment also features a vertical distance gap 19 between the peaks 158 and the outflow end of the valve enclosure 145, for allowing the wall inset 158 freedom in moving vertically, unconstrained by the valve enclosure 145.

Since the maximum deflection of the wall inset 158 occurs at the peaks 159, this fashion of mounting the valve allows it to function in its normal free state, while also mounted in a rigid structure.

The inflow and outflow base rings 146 and 147, as well as the vertical legs 149, are provided with holes 20, 25 and 30, respectively, for suturing the movable wall 152 onto the valve enclosure assembly 141 in a manner which will be described below.

FIGS. 4A, 4D, 4E and 4F show the inflow suture assembly 150, which comprises an inflow suture ring cover 151. The inflow suture ring cover 151 is a rigid ring. It has holes 15 for stitching the tissue valve 300. The inflow suture ring cover 151 corresponds to the inflow base ring 146 of the valve enclosure 145 (FIG. 4C). The inflow base ring 146 is wrapped by the suture ring cover 151 around it. The inflow suture ring cover 151 is made from a blood compatible fabric material to be stitched around the inflow base ring 146, in order to provide an inflow suturing support for the movable wall 152.

Turning back to FIG. 4A, the outflow suture assembly 142 is sutured onto the outflow base ring 147 of the valve enclosure 145, forming a flange 26. Flange 26 is designed to fit smoothly into the inflow elbow assembly 170 of FIG. 2A. The two ends of the valve assembly 140 are distinguished by the flange 26. The flange 26 is matingly adapted only in one direction into the elbow assembly 170. Thus, the valve assembly 140 can be installed within assembly 100 in only one way. This feature eliminates the risks of wrongly connecting the valves in the conduits in a wrong direction. The provision of the flange 26 leads to an easier, safer fitting procedure.

The outflow suture ring 143 is a rigid ring, of mating size with the outflow base ring 147 of the valve enclosure 145. The outflow suture ring 143 provides an outflow suturing support for the movable wall 152 in assembling the valve assembly 140.

Referring to FIGS. 4A–4E, the valve assembly 140 is assembled as follows:

First, the valve enclosure assembly 141 is assembled, by attaching the inflow suture assembly 150 to the outflow suture assembly 142. As described above, the inflow suture assembly 150 comprises the valve enclosure 145 with the inflow suture ring cover 151 wrapped around the inflow base ring 146 of the valve enclosure 145. The outflow suture assembly 142 comprises the outflow suture ring 143 with the outflow suture ring cover 144 wrapped around it.

Second, the movable wall 152 is placed inside the assembled valve enclosure assembly 141 with its inflow end facing the inflow side of the valve enclosure assembly 141.

Third, the inflow end 153 of the grafted fabric 156 is stitched on the circumference of the inflow suture support provided by the inflow suture ring cover 151 of the inflow suture assembly 150.

Finally, the outflow end 154 of the grafted fabric 156 is stitched on the circumference of the outflow suture support provided by the outflow suture ring cover 144 of the outflow suture assembly 142.

In a preferred embodiment, the suturing technique is such that the suturing material, which may be thrombogenic, does not come into contact with the blood flowing through the conduit assembly. Thus, stitching occurs only on surfaces that do not contact the main blood flow stream, when in operation. A method of assembling the valve assembly 140 and its subassemblies, in accordance with such a preferred embodiment, is described in detail next.

Assembling the Outflow Suture Assembly

Figure 4D:
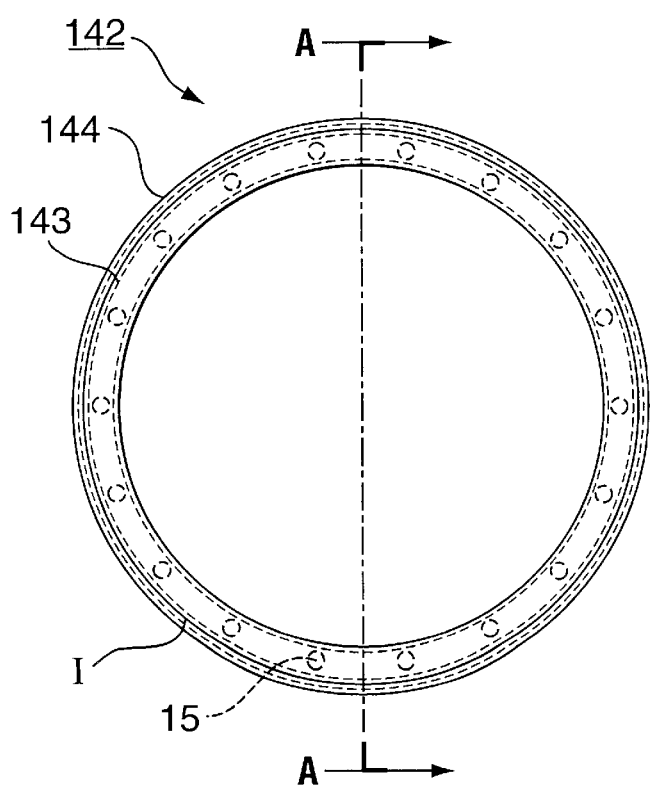
FIG. 4D is a bottom cross-sectional view of the outflow suture assembly in accordance with the embodiment in FIG. 4A.
Figure 4E:
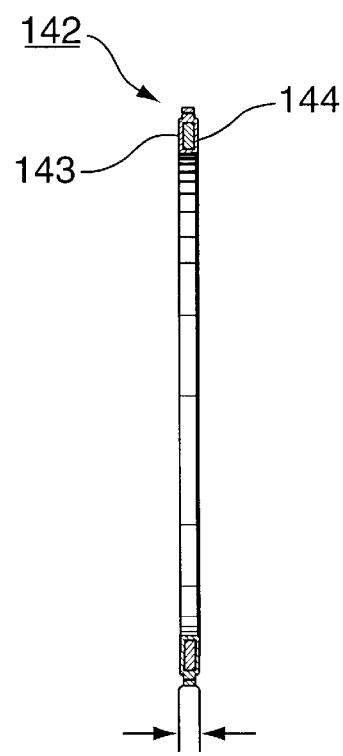
FIG. 4E is a cross-sectional view of the outflow suture assembly in FIG. 4D.
Figure 4F:
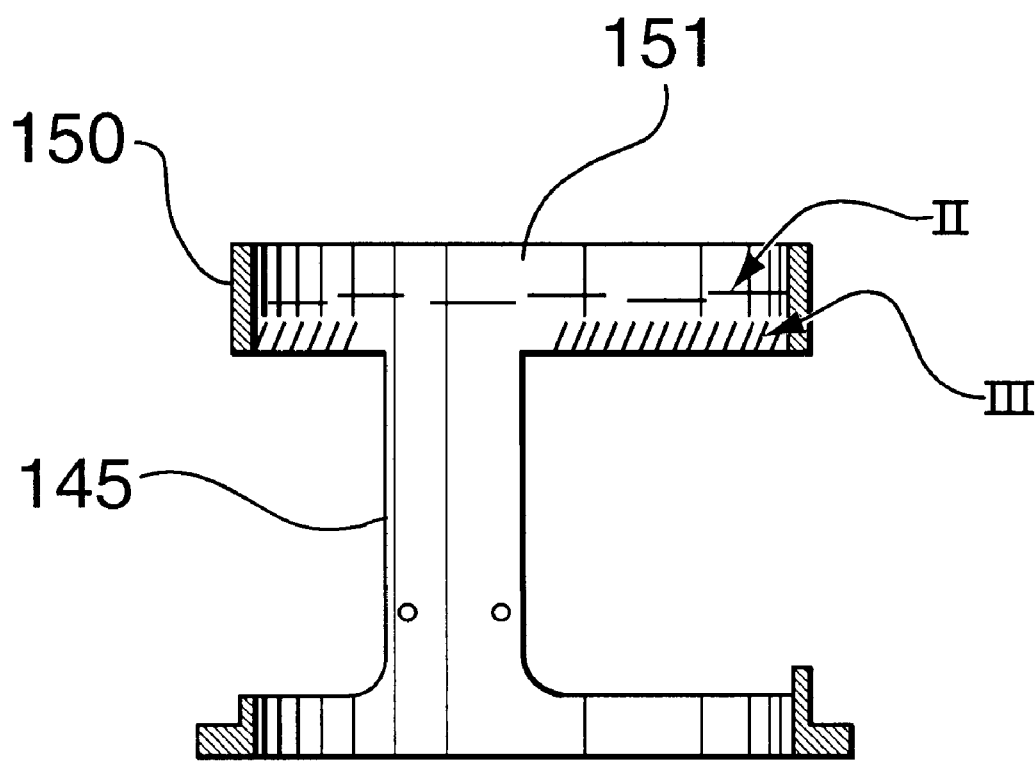
FIG. 4F is a lateral cross-sectional view of the inflow suture assembly in accordance with the embodiment in FIG. 4A.

Referring now more specifically to FIGS. 4D and 5B and as previously described, the outflow suture assembly 142 provides a suturing support on the outflow end of the valve enclosure assembly 141, for the modified tissue valve 152. The support is provided through the outflow suture ring cover 144 which has to be wrapped and sutured around the outflow suture ring 143. The ring of sutures around the periphery of the outflow suture assembly 142 thus obtained is herein denoted by I.

According to a preferred embodiment of the invention, the assembling of the outflow suture assembly 142 comprises the following substeps:

1. A rectangular strip of a biocompatible fabric is cut at a suitable size, for forming the outflow suture ring cover 144.
2. The fabric forming the outflow suture ring cover 144 is wrapped around and held tight against the inside surface of the outflow suture ring 143 with the excess material lying outside the outflow suture ring 143.
3. Using a surgical suture, a first stitch is made at the edge of the fabric forming outflow suture ring cover 144. When passing the needle, one should preferably make sure that it is directly against the outer surface of the outflow suture ring 143 through both the upper and lower layer of the outflow suture ring cover 144. The initial knot is started by passing the needle through the two layers twice in the same location. During the second pass, while the needle is still part way through the outflow suture ring cover 144, the suture line is wrapped around the needle twice, the needle is pulled through the double loop, and then the knot is tightened.
4. A stitch is passed back through both layers of the outflow suture ring cover 144 with a stitch length of 5+/−1 mm, still being careful to have the needle directly against the outer surface of the outflow suture ring 143. Reversing the stitch direction, a stitch is made back through where the stitch initially started. When the stitch comes through the outflow suture cover ring 144, one makes sure the stitch passes between the previous stitch and the outflow suture ring 143 so that the suture line is not cut by the needle and the stitch remains tight.
5. A stitch is passed through both layers of the outflow suture ring cover 144 with a stitch length of 7+/−1 mm.
6. With a stitch length of 5+/−1 mm, the direction is reversed and a stitch is passed through the outflow suture ring 143. A cover is made so that the suture emerges near the previous stitch. Again, for the reverse direction stitch, the needle is passed between the previous suture line and the outflow suture ring 143.
7. The sutures are continued with a stitch length of 5+/−1 mm, continuously ensuring that the outflow suture ring cover 144 stays tight against the inside surface of the outflow suture ring 143.
8. Once the outflow suture ring cover 144 has been sutured around the entire circumference of the outflow suture ring 143, the outflow suture ring cover 144 is cut to length such that the two edges of the outflow suture ring cover 144 abut against each other.
9. Two additional stitches are made across the gap in the outflow suture ring cover 144, then the suture is tied off with two double finishing knots, a final stitch is passed underneath the knot with each line and then cut the suture at the surface of the outflow suture ring cover 144 using the surgical scissors with the rounded cutting edge.

10. The outflow suture ring cover 144 is cut 1.0–2.0 mm outside of the periphery of the completed ring of sutures.
11. Using a soldering iron set to 277+/−10° C., the seam is welded along the two edges of the outflow suture ring cover 144 starting at the interior surface and working in the radial direction, being careful not to touch the suture material which could melt and break upon contact.
12. In a similar manner, the soldering iron set to 277+/−10° C. is used to weld the seam along the outer periphery of the outflow suture ring assembly 142.

Assembling the Inflow Suture Assembly

Referring now more specifically to FIGS. 4A, 4C, 4F and 5A and previously described, the inflow suture assembly 150 provides a suturing support on the inflow end of the valve enclosure assembly 141. The support is provided by the inflow suture ring cover 151 which has to be wrapped and sutured around the inflow base ring 146 of the valve enclosure 145. According to a preferred embodiment of the invention, the assembling of the inflow suture assembly 150 comprises the following substeps:

A) A first ring of sutures II is made in order to attach the inflow suture ring cover 151 to the inflow base ring 146 of the valve enclosure 145, by passing a surgical suture through the holes 20 in the inflow base ring 146. In detail, this may be done as follows:

1. A piece of uncrimped fabric shaped into a conduit having a diameter approximately equal to the diameter of the movable wall 152 and to the internal diameter of the valve enclosure 145, is fed through the valve enclosure 145 and wrapped around the inflow base ring 146 of the valve enclosure 145 such that 5.0+/−1.0 mm is hanging over the outside portion of the valve enclosure 145 and the remainder of the uncrimped fabric conduit is within the valve enclosure 145. In this embodiment, the uncrimped fabric conduit forms the inflow suture ring cover 151.
2. A cylindrical rubber stopper is placed into the valve enclosure's 145 inflow orifice to hold the inflow suture ring cover 151 in place.
3. Using a surgical suture, the suturing of the inflow suture ring cover 151 to the valve enclosure 145 is started through one of the holes 20 in the inflow base ring 146. Preferably, this stitch should start from the outside traveling towards the inside.
4. The suture is then taken through the adjacent hole 20 from the inside out.
5. The two ends of the sutures are tied off with two double knots that are made on the inflow suture ring cover 151 in between two holes 20 on the inflow base ring 146 on the external surface of the valve enclosure 145. The sutures are tied off such that there are approximately equal lengths of suture on either side of the knot.
6. The knot is tightened so that it resides over one of the two holes 20 in the inflow base ring 146 that have just been tied off.
7. The next suture is started with the last hole 20 that was used coming from the outside in and then bringing the suture back out in the adjacent hole 20 in a similar manner as before.
8. Continue making sutures until all holes 20 are stitched.
9. Once the final knot has been tied around the periphery of the component, the two ends of the suture are left as they will be used later.

B) A second ring of sutures III is made in order to suture the inflow suture ring cover 151 closed where the two portions of the fabric conduit come together. In detail, this may be done as follows:

10. The fabric conduit making the inflow suture ring cover 151 is cut to the same length on the internal side of the valve enclosure 145 as the fabric is overhanging on the external side of the valve enclosure 145.
11. The suture line is passed underneath the external layer of the fabric conduit so that it emerges near the edge of the uncrimped fabric conduit using the longer portion of the suture left from point 9. Then, starting from the outside and working towards the center, a stitch is passed through both layers of the conduit uncrimped fabric to start the stitch.
12. As the stitch is being made, a knot is tied to complete each stitch. This can be done by wrapping the suture line around the needle before the needle is completely pulled through the material.
13. The suturing is continued around the periphery of the uncrimped fabric conduit with 3–5 mm long stitches located on average ~2.0–2.5 mm apart.
14. When crossing between two of the windows 148 in the valve enclosure 145, a single stitch is made, that starts at one edge of the window that has just been completed, which passes under the fabric conduit on the external side of the valve enclosure 145, and emerges at the edge of the next window 148 on the valve enclosure 145.
15. The suture is finished off by making a single stitch back down near the original knot at the bottom of the fabric conduit and then make two double knots, and then feeding the two ends of the suture through the fabric under the knot, and then cutting the ends of the suture.
16. Once the suture is completed around the base of the uncrimped fabric conduit making the inflow suture ring cover 151, a soldering iron at 277+/−10° C. is used to weld the seam shut, being careful not to contact the suture which could melt.

Assembling the Valve Enclosure Assembly

Referring now more specifically to FIGS. 4C, 4D and 5B, as previously described, the assembling of the valve enclosure assembly 141 consists in attaching the inflow suture assembly 150 and the outflow suture assembly 142 together. In this embodiment, this is accomplished by the suture technique described in detail below, the result of which is a new ring of sutures IV, obtained by passing a suture through the holes 15 in the outflow suture assembly 142 and the holes 25 in the outflow base ring 147 of the valve enclosure 145.

1. The assembled outflow suture ring assembly 142 is positioned over the outflow base ring 147 of the valve enclosure 145, so that their sets of holes, 15 and 25, respectively, overlap.
2. Using a surgical suture, the suture is started by passing a stitch through the holes 15 in the outflow suture ring assembly 142 and through the holes 25 in the outflow base ring 147 of the valve enclosure 145 and then passing the other needle through the adjacent pair of holes 15, 25 in the outflow suture ring assembly 142 and the outflow base ring 147, respectively.
3. The two free ends are tied with two double knots and the resulting knot is located directly over one of the hole-pairs 15, 25.
4. One end of the suture is passed through the hole-pair 15, 25 where the last knot was located and the suture is brought back through the adjacent hole-pair 15, 25.

5. The two loose ends of the suture are tied off with two double knots and the knot is located directly over the holes 15, 25.
6. The suturing of the outflow suture ring assembly 142 to the valve enclosure assembly 141 is continued through the eighteen hole-pairs 15, 25.
7. Once the suturing is completed, the suture line is passed down through the last hole 25 of the valve enclosure 145 but not through the corresponding hole 15 of the outflow suture ring assembly 142. The suture line is passed between the valve enclosure 145 and the outflow suture ring assembly 142 to the outside edge of the components. The suture is tied off on the outside edge of the outflow suture ring assembly 142 so that the knot is not located on the flat bottom of the component.
8. After the knot is tied, a stitch is passed under the knot and then the suture is cut close to the surface using the surgical scissors with the rounded cutting edge.

Assembling the Valve Assembly

Referring now to FIGS. 4A, 4B, 5A and 5B and as previously described, the final steps in assembling the valve assembly are the suturing of the movable wall 152 inside the assembled valve enclosure assembly 141. This involves three main steps, as described next:

A) The movable wall 152 is placed inside the assembled valve enclosure assembly 141 with its inflow end facing the inflow side of the valve enclosure assembly 141. In detail, this can be accomplished as follows:
 1. A suitable movable wall 152 as previously described is removed from sterile water and its grafted fabric 156, shaped into a conduit, is cut approximately 5 corrugations above and below the tissue valve, 153, 154.
 2. The movable wall 152 is then inserted into the assembled valve enclosure assembly 141 such that each of the peaks 159 of the wall inset 158 lies centered within the window 148 of the valve enclosure 145 and the peak 159 of the wall inset 158 lies 1–2 mm above the outflow side of the window 148 of the valve enclosure 149. The movable wall 152 is in the proper orientation when the peaks 159 of the valve leaflets are pointing towards that outflow suture ring assembly 142.

B) The inflow end 153 of the grafted fabric 156 is stitched on the circumference of the inflow suture support provided by the inflow suture ring cover of the inflow suture assembly 150 by creating a new ring of sutures V. In detail, this can be accomplished as follows:
 3. The movable wall 152 is trimmed so that it is flush to the base surface of the inflow orifice of the valve enclosure assembly 141. The inflow orifice should preferably be approximately 1.5 corrugations 153 above the inset 158 of the movable wall 152, as shown in FIG. 4B.
 4. While ensuring to keeping the fabric taut, using a surgical suture, the stitch starts by passing a suture from the outer periphery of the valve enclosure assembly 141, through the inflow suture ring cover 151 and back out through the movable wall 152, as close to the valve enclosure 145 as possible, and then a double knot is made. Preferably the knot should be located on the outside edge of the valve assembly 140.
 5. A continuous stitch, forming a new ring of sutures V, with stitches approximately 5 mm long and 2–3 mm apart is made around the inflow periphery of the valve enclosure assembly 141, making sure that the stitch lies on the upper surface of the valve enclosure assembly 141, for a total of approximately 30–50 stitches.
 6. Once the continuous stitch has returned to the starting position, it shall be tied off with the starting loose end using two double knots.
 7. After the knot has been tied, both loose ends of the suture are passed through the uncrimped conduit, under the knot and then cut with the surgical scissors with the rounded cutting edge.

C) The outflow end of the grafted fabric 156 is stitched on the circumference of the outflow suture support provided by the outflow suture ring cover of the outflow suture assembly 142, by creating a new ring of sutures VI. In detail, this can be accomplished as follows:
 9. The valve assembly 140 is turned over and the outflow orifice of the modified tissue valved 152 is trimmed down flush to the outflow suture ring 143 surface using the scalpel, leaving approximately 2.5 graft corrugations 154 between the peaks 159 of the wall inset 158 and the end of the fabric 156 of the movable wall 152.
 10. Using a surgical suture a stitch is started by passing the suture line from the outside of the valve assembly 140, in through the outflow suture ring assembly 142 and out through the fabric 156 of the movable wall 152. This stitch should be made in between the ring of suture IV holding the outflow suture ring assembly 142 to the valve enclosure 145 and the ring of suture I holding the outflow suture ring assembly 142 together.
 11. A continuous stitch, forming a new ring of sutures VI, is made with stitches approximately 5 mm in length and 2–3 mm apart around the outflow orifice (for a total of 30–50 stitches) ensuring that the stitch is made on the flat surface of the outflow suture ring assembly 142. Care must be taken to ensure the grafted fabric 156 conduit is stretched to fit the valve enclosure 145.
 12. The suture is finished in a manner similar to that described above for the assembling of the inflow suture assembly 150 in steps 7–9.

D) In this embodiment, the movable wall 152 is also attached midways to the valve enclosure, by suturing its grafted fabric to the legs 149 of the valve enclosure, through the holes 30 provided in the legs. In more detail, this can be accomplished as follows:
 13. The final sutures will be done through the holes 30 in the legs 149 of the valve enclosure 145.
 14. A stitch is passed from the outside of the valve enclosure 145, through one of the holes 30 and the modified valved conduit and then back out the adjacent hole 30.
 15. The two free ends of the suture are tied with three double knots and then the free ends of the suture will be cut off leaving approximately 3 mm of length at the end of the lines.
 16. Steps 14–15 are repeated for all three sets of holes 30 in the legs 149 of the valve enclosure 145.

E) The valve enclosure 145 is visually inspected, and stored in a container.

F) A small portion of the graft conduit 156 that was trimmed off at substep 3 (approximately 1×2 cm) is cut and placed this into the container with the valve assembly 140 for future bacteria cultures.

Although a suturing technique has been described above in detail, it will to be appreciated by one skilled in the art that this description only pertains to a specific embodiment of the invention. Other suturing techniques may be employed for the assembling of the various components and for attaching the movable wall 152 to the valve enclosure assembly 141. Moreover, other methods of attachment known in the art, such as glueing, can be used in assembling the various parts of the valve assembly 140 together.

Turning back to FIG. 2A, the valve assembly 140 is mounted on the inflow conduit assembly 100 by sliding its inflow end into enlarged elongated cylindrical opening of the apical tip assembly 110, and its outflow end with flange 26 into the inflow elbow assembly 170.

Referring now to FIG. 2B, as indicated above, the outflow valve assembly 240 is identical in structure to the inflow valve assembly 140. The outflow valve assembly 240 is mounted into the outflow conduit assembly 200 by sliding its outflow end with flange 27 into the outflow conduit 210 and its inflow end into enlarged elongated cylindrical opening of outflow elbow assembly 270.

Numerous modifications, variations, and adaptations must be made to the particular embodiments of the invention described above, without departing from the scope of the invention, which is defined in the claims.

What is claimed is:

1. An inflow conduit assembly for conducting blood from a ventricle to a Ventricular Assist Device (VAD), the inflow conduit assembly comprising a rigid tube comprising an angled heart engaging end for insertion into a ventricle, the angled heart engaging end defining a long side for placement adjacent a heart septum, and the angled heart engaging end having an outer surface defining at least one hole for draining blood from the ventricle.

2. An inflow conduit assembly as defined in claim 1, wherein the tube comprises an orifice end for attachment to the VAD, the inflow conduit assembly further comprising a coupling for attaching the orifice end of the tube to the VAD, the coupling being movable between a rotatable position wherein the tube is rotatable relative to the VAD, and a locked position wherein the tube is immobile relative to the VAD.

3. An inflow conduit assembly as defined in claim 2, wherein:
   a. the tube comprises an outer surface comprising a thread adjacent the orifice end;
   b. the coupling comprises a gland nut for engaging the thread and a corresponding thread on or attached to the MCD, the gland nut being movable between a rotatable position wherein the tube is rotatable relative to the MCD, and a locked position wherein the tube is immobile relative to the MCD.

4. An inflow conduit assembly as defined in claim 3, wherein the tube is circular in cross-section.

5. An inflow conduit assembly as defined in claim 1, wherein the outer surface of the angled heart engaging end defines a plurality of holes.

6. An inflow conduit assembly as defined in claim 5, wherein the holes are arranged annularly around the heart engaging end.

7. An inflow conduit assembly as defined in claim 1, wherein the at least one hole has a diameter sufficiently large to avoid blood clotting.

8. An inflow conduit assembly as defined in claim 7, wherein the diameter of the at least one hole is about 3 millimeters.

9. An inflow conduit assembly as defined in claim 1, wherein the tube comprises an inner surface adapted to receive a valve assembly.

10. An inflow conduit assembly as defined in claim 1, wherein the tube comprises a straight section comprising an inner surface adapted to receive a valve assembly.

11. An inflow conduit assembly as defined in claim 1, wherein the tube comprises an outer surface, the conduit assembly further comprising a pliable annular skirt attached to the outer surface of the tube, the skirt being attachable by suturing to the outside of a heart.

12. An inflow conduit assembly as defined in claim 1, wherein the tube is constructed of oxidized titanium.

13. An inflow conduit assembly as defined in claim 1, wherein the tube is constructed of titanium.

14. An inflow conduit assembly for conducting blood from a ventricle to a Ventricular Assist Device (VAD), the inflow conduit assembly comprising a rigid tube comprising an angled heart engaging end for insertion into a ventricle, the angled heart engaging end defining a long side for placement adjacent a heart septum, and the angled heart engaging end having an outer surface having means for draining blood from the ventricle.

15. A method for implanting a circulatory apparatus in a patient, the apparatus comprising a Ventricular Assist Device (VAD) having an orifice, and an inflow conduit assembly for attachment to the Ventricular Assist Device (VAD), the inflow conduit assembly comprising: a rigid tube comprising an angled heart engaging end for insertion into a ventricle, the angled heart engaging end defining a long side for placement adjacent a heart septum and the angled heart engaging end having a outer wall defining at least a hole; and a coupling for attaching the orifice end of the tube to the Ventricular Assist Device (VAD), the coupling being movable between a rotatable position wherein the tube is rotatable relative to the Ventricular Assist Device (VAD), and a locked position wherein the tube is immobile relative to the Ventricular Assist Device (VAD), the method comprising the steps of:
   a. moving the coupling to the rotatable position;
   b. positioning the Ventricular Assist Device (VAD) relative to the patient;
   c. rotating the tube until the desired position of the long side of the angled heart engaging end is achieved;
   d. moving the coupling to the locked position;
   e. inserting the heart engaging end into a ventricle such that the long side is adjacent a heart septum; and
   f. locating the at least hole within the ventricle for draining blood from the ventricle.

* * * * *